(12) United States Patent
Fangrow, Jr.

(10) Patent No.: US 8,398,607 B2
(45) Date of Patent: Mar. 19, 2013

(54) MEDICAL CONNECTOR

(75) Inventor: Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 13/361,499

(22) Filed: Jan. 30, 2012

(65) Prior Publication Data

US 2012/0245551 A1   Sep. 27, 2012

Related U.S. Application Data

(63) Continuation of application No. 11/924,494, filed on Oct. 25, 2007, now Pat. No. 8,105,314.

(60) Provisional application No. 60/854,524, filed on Oct. 25, 2006.

(51) Int. Cl.
*A61M 31/00* (2006.01)

(52) U.S. Cl. ............... 604/500; 604/537; 251/149.1

(58) Field of Classification Search ............... 604/246, 604/247, 249, 256, 500, 506–508, 511, 513, 604/533–535, 537; 251/149.1, 149.4, 149.6, 251/149.7
See application file for complete search history.

(56) References Cited

U.S. PATENT DOCUMENTS

| 274,447 | A | 3/1883 | Kennish |
|---|---|---|---|
| 1,578,517 | A | 3/1926 | Hein |
| 1,923,501 | A | 8/1933 | Perry |
| 2,210,098 | A | 8/1940 | Ravenscroft |
| 2,289,677 | A | 7/1942 | Perelson |
| 2,577,780 | A | 12/1951 | Lockhart |
| 2,756,282 | A | 7/1956 | Deane |
| 2,756,740 | A | 7/1956 | Deane |
| 2,809,665 | A | 10/1957 | Crowe |
| 2,847,995 | A | 8/1958 | Adams |
| 2,999,499 | A | 9/1961 | Willet |
| 3,134,380 | A | 5/1964 | Armao |
| 3,135,261 | A | 6/1964 | Carroll |
| 3,171,412 | A | 3/1965 | Braun |
| 3,176,021 | A | 3/1965 | Volungis et al. |
| 3,191,655 | A | 6/1965 | McCord |
| 3,193,154 | A | 7/1965 | Bross et al. |
| 3,334,860 | A | 8/1967 | Bolton, Jr. |
| 3,352,531 | A | 11/1967 | Kilmarx |
| 3,354,881 | A | 11/1967 | Bloch |
| 3,385,301 | A | 5/1968 | Harautuneian |

(Continued)

FOREIGN PATENT DOCUMENTS

| CA | 1 105 959 | 7/1981 |
|---|---|---|
| CA | 2 149 725 | 11/1995 |

(Continued)

OTHER PUBLICATIONS

U.S. Appl. No. 08/767,587, filed Dec. 16, 1996, Lopez et al.

(Continued)

*Primary Examiner* — Kevin C Sirmons
*Assistant Examiner* — Kami A Bosworth
(74) *Attorney, Agent, or Firm* — Knobbe, Martens, Olson & Bear LLP

(57) ABSTRACT

A medical connector for use with one or more medical implements. In some embodiments, the connector minimizes or eliminates the retrograde flow of fluid into the connector from one end or port upon the disconnection of a medical implement from the other end or port. In some embodiments, the connector generates a positive flow of fluid out of the connector from one end or port when a medical implement is disconnected from the other end or port.

7 Claims, 10 Drawing Sheets

U.S. PATENT DOCUMENTS

| | | |
|---|---|---|
| 3,502,097 A | 3/1970 | Muller |
| 3,534,771 A | 10/1970 | Eyerdam et al. |
| 3,570,484 A | 3/1971 | Steer et al. |
| 3,630,199 A | 12/1971 | Gangarosa |
| 3,648,684 A | 3/1972 | Barnwell et al. |
| 3,659,602 A | 5/1972 | Cloyd |
| 3,717,174 A | 2/1973 | Dewall |
| 3,726,282 A | 4/1973 | Patel |
| 3,788,519 A | 1/1974 | Mengel |
| 3,830,241 A | 8/1974 | Dye et al. |
| 3,831,629 A | 8/1974 | Mackal et al. |
| 3,852,385 A | 12/1974 | Huggins |
| 3,861,388 A | 1/1975 | Vaughn |
| 3,889,675 A | 6/1975 | Stewart |
| 3,896,853 A | 7/1975 | Bernhard |
| 3,965,910 A | 6/1976 | Fisher |
| 3,974,832 A | 8/1976 | Kruck |
| 3,976,063 A | 8/1976 | Henneman et al. |
| 3,976,073 A | 8/1976 | Quick et al. |
| 3,977,403 A | 8/1976 | Patel |
| 3,986,508 A | 10/1976 | Barrington |
| 3,993,063 A | 11/1976 | Larrabee |
| 3,994,293 A | 11/1976 | Ferro |
| 4,005,710 A | 2/1977 | Zeddies et al. |
| 4,019,512 A | 4/1977 | Tenczar |
| 4,022,205 A | 5/1977 | Tenczar |
| 4,040,420 A | 8/1977 | Speer |
| 4,076,285 A | 2/1978 | Martinez |
| 4,079,738 A | 3/1978 | Dunn et al. |
| 4,080,965 A | 3/1978 | Phillips |
| 4,121,585 A | 10/1978 | Becker, Jr. |
| 4,128,098 A | 12/1978 | Bloom et al. |
| 4,133,441 A | 1/1979 | Mittleman et al. |
| 4,143,853 A | 3/1979 | Abramson |
| 4,149,535 A | 4/1979 | Volder |
| 4,161,949 A | 7/1979 | Thanawalla |
| 4,186,775 A | 2/1980 | Muroi |
| 4,187,846 A | 2/1980 | Lolachi et al. |
| 4,191,183 A | 3/1980 | Mendelson |
| 4,198,983 A | 4/1980 | Becker et al. |
| 4,200,096 A | 4/1980 | Charvin |
| 4,214,779 A | 7/1980 | Losell |
| 4,219,912 A | 9/1980 | Adams |
| 4,243,034 A | 1/1981 | Brandt |
| 4,257,416 A | 3/1981 | Prager |
| D259,278 S | 5/1981 | McCaw et al. |
| 4,294,249 A | 10/1981 | Sheehan et al. |
| 4,294,250 A | 10/1981 | Dennehey |
| 4,296,949 A | 10/1981 | Muetterties et al. |
| 4,306,705 A | 12/1981 | Svensson |
| 4,324,239 A | 4/1982 | Gordon et al. |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard et al. |
| 4,342,315 A | 8/1982 | Jackson |
| 4,346,703 A | 8/1982 | Dennehey et al. |
| 4,362,156 A | 12/1982 | Feller et al. |
| 4,387,879 A | 6/1983 | Tauschinski |
| RE31,315 E | 7/1983 | Jenkins et al. |
| 4,392,851 A | 7/1983 | Elias |
| 4,405,163 A | 9/1983 | Voges et al. |
| 4,405,312 A | 9/1983 | Gross et al. |
| 4,411,662 A | 10/1983 | Pearson |
| 4,417,890 A | 11/1983 | Dennehey et al. |
| 4,421,296 A | 12/1983 | Stephens |
| 4,429,856 A | 2/1984 | Jackson |
| 4,432,759 A | 2/1984 | Gross et al. |
| 4,432,765 A | 2/1984 | Oscarsson |
| 4,439,188 A | 3/1984 | Dennehey et al. |
| 4,439,193 A | 3/1984 | Larkin |
| 4,449,693 A | 5/1984 | Gerea |
| 4,457,749 A | 7/1984 | Bellotti et al. |
| 4,483,368 A | 11/1984 | Panthafer |
| 4,508,367 A | 4/1985 | Oreopoulos et al. |
| 4,511,359 A | 4/1985 | Vaillancourt |
| 4,512,766 A | 4/1985 | Vailancourt |
| 4,564,054 A | 1/1986 | Gustavsson |
| 4,592,356 A | 6/1986 | Gutierrez |
| 4,607,868 A | 8/1986 | Harvey et al. |
| 4,610,469 A | 9/1986 | Wolff-Mooij |
| 4,617,012 A | 10/1986 | Vaillancourt |
| 4,619,640 A | 10/1986 | Potolsky et al. |
| 4,623,068 A | 11/1986 | Brown et al. |
| 4,645,494 A | 2/1987 | Lee et al. |
| 4,666,429 A | 5/1987 | Stone |
| 4,673,400 A | 6/1987 | Martin |
| 4,676,228 A | 6/1987 | Krasner et al. |
| 4,683,916 A | 8/1987 | Raines |
| 4,706,487 A | 11/1987 | Bandou et al. |
| 4,710,168 A | 12/1987 | Schwab et al. |
| 4,725,267 A | 2/1988 | Vaillancourt |
| 4,730,635 A | 3/1988 | Linden |
| 4,752,292 A | 6/1988 | Lopez et al. |
| D296,592 S | 7/1988 | Wellenstam |
| 4,758,224 A | 7/1988 | Siposs |
| 4,759,756 A | 7/1988 | Forman et al. |
| 4,775,369 A | 10/1988 | Schwartz |
| 4,778,447 A | 10/1988 | Velde et al. |
| 4,778,453 A | 10/1988 | Lopez |
| 4,781,702 A | 11/1988 | Herrli |
| 4,804,015 A | 2/1989 | Albinsson |
| D300,177 S | 3/1989 | Bellotti et al. |
| 4,810,241 A | 3/1989 | Rogers et al. |
| 4,813,938 A | 3/1989 | Raulerson |
| 4,819,684 A | 4/1989 | Zaugg et al. |
| 4,832,214 A | 5/1989 | Schrader et al. |
| 4,834,664 A | 5/1989 | Lin |
| 4,834,716 A | 5/1989 | Ogle, II |
| D303,013 S | 8/1989 | Konopka |
| 4,874,377 A | 10/1989 | Newgard et al. |
| 4,878,897 A | 11/1989 | Katzin |
| 4,880,414 A | 11/1989 | Whipple |
| 4,889,527 A | 12/1989 | Herrli |
| 4,915,687 A | 4/1990 | Sivert |
| 4,917,668 A | 4/1990 | Haindl |
| 4,919,167 A | 4/1990 | Manska |
| 4,928,212 A | 5/1990 | Benavides |
| 4,934,657 A | 6/1990 | Dodson |
| 4,943,896 A | 7/1990 | Johnson |
| 4,946,445 A | 8/1990 | Lynn |
| 4,963,133 A | 10/1990 | Whipple |
| 4,964,855 A | 10/1990 | Todd et al. |
| 4,966,199 A | 10/1990 | Ruschke |
| 4,969,883 A | 11/1990 | Gilbert et al. |
| D314,050 S | 1/1991 | Sone |
| 4,985,399 A | 1/1991 | Matsuda et al. |
| 4,987,181 A | 1/1991 | Bichon et al. |
| 4,991,413 A | 2/1991 | Arnalda |
| 4,991,629 A | 2/1991 | Ernesto et al. |
| 4,998,713 A | 3/1991 | Vaillancourt |
| 4,998,927 A | 3/1991 | Vaillancourt |
| 5,006,114 A | 4/1991 | Rogers et al. |
| 5,009,490 A | 4/1991 | Kouno et al. |
| 5,018,532 A | 5/1991 | Etheredge, III |
| 5,024,657 A | 6/1991 | Needham et al. |
| 5,031,675 A | 7/1991 | Lindgren |
| 5,041,087 A | 8/1991 | Loo et al. |
| 5,046,456 A | 9/1991 | Heyman et al. |
| 5,049,128 A | 9/1991 | Duquette |
| D321,250 S | 10/1991 | Jepson et al. |
| D321,251 S | 10/1991 | Jepson et al. |
| 5,061,253 A | 10/1991 | Yoshida |
| 5,064,416 A | 11/1991 | Newgard et al. |
| 5,065,783 A | 11/1991 | Ogle, II |
| 5,071,411 A | 12/1991 | Hillstead |
| 5,098,385 A | 3/1992 | Walsh |
| 5,098,405 A | 3/1992 | Peterson et al. |
| 5,098,406 A | 3/1992 | Sawyer |
| 5,100,394 A | 3/1992 | Dudar et al. |
| 5,108,380 A | 4/1992 | Herlitze et al. |
| 5,114,408 A | 5/1992 | Fleischhaker et al. |
| 5,116,361 A | 5/1992 | Kim et al. |
| 5,122,123 A | 6/1992 | Vaillancourt |
| 5,125,915 A | 6/1992 | Berry et al. |
| 5,135,489 A | 8/1992 | Jepson et al. |
| 5,137,524 A | 8/1992 | Lynn et al. |

| Patent | Date | Inventor |
|---|---|---|
| 5,147,333 A | 9/1992 | Raines |
| 5,154,703 A | 10/1992 | Bonaldo |
| 5,158,554 A | 10/1992 | Jepson et al. |
| 5,163,922 A | 11/1992 | McElveen, Jr. et al. |
| 5,167,238 A | 12/1992 | Newman |
| 5,167,636 A | 12/1992 | Clement |
| 5,171,234 A | 12/1992 | Jepson et al. |
| 5,180,761 A | 1/1993 | Shiao |
| 5,188,620 A | 2/1993 | Jepson et al. |
| 5,190,067 A | 3/1993 | Paradis et al. |
| 5,199,947 A | 4/1993 | Lopez et al. |
| 5,201,717 A | 4/1993 | Wyatt et al. |
| 5,201,722 A | 4/1993 | Moorehead et al. |
| 5,203,775 A | 4/1993 | Frank et al. |
| 5,211,638 A | 5/1993 | Dudar et al. |
| 5,215,538 A | 6/1993 | Larkin |
| 5,221,271 A | 6/1993 | Nicholson et al. |
| 5,224,515 A | 7/1993 | Foster et al. |
| 5,242,393 A | 9/1993 | Brimhall et al. |
| 5,242,423 A | 9/1993 | Goodsir et al. |
| 5,242,425 A | 9/1993 | White et al. |
| 5,242,432 A | 9/1993 | DeFrank |
| 5,251,873 A | 10/1993 | Atkinson et al. |
| 5,253,842 A | 10/1993 | Huebscher et al. |
| 5,255,676 A | 10/1993 | Russo |
| 5,256,155 A | 10/1993 | Yerlikaya et al. |
| 5,267,966 A | 12/1993 | Paul |
| 5,269,771 A | 12/1993 | Thomas et al. |
| 5,273,533 A | 12/1993 | Bonaldo |
| 5,280,876 A | 1/1994 | Atkins |
| 5,284,475 A | 2/1994 | Mackal |
| 5,290,254 A | 3/1994 | Vaillancourt |
| 5,292,308 A | 3/1994 | Ryan |
| 5,293,902 A | 3/1994 | Lapierie |
| 5,295,657 A | 3/1994 | Atkinson |
| 5,295,658 A | 3/1994 | Atkinson et al. |
| 5,301,686 A | 4/1994 | Newman |
| 5,306,265 A | 4/1994 | Ragazzi |
| 5,312,083 A | 5/1994 | Ekman |
| 5,312,377 A | 5/1994 | Dalhon |
| 5,322,518 A | 6/1994 | Schneider |
| 5,324,270 A | 6/1994 | Kayon et al. |
| 5,336,192 A | 8/1994 | Palestrant |
| 5,342,316 A | 8/1994 | Wallace |
| 5,342,326 A | 8/1994 | Peppel et al. |
| 5,344,414 A | 9/1994 | Lopez et al. |
| 5,348,542 A | 9/1994 | Ellis |
| 5,353,837 A | 10/1994 | Faust |
| 5,356,396 A | 10/1994 | Wyatt et al. |
| 5,360,413 A | 11/1994 | Leason et al. |
| 5,380,306 A | 1/1995 | Brinon |
| 5,389,086 A | 2/1995 | Attermeier et al. |
| 5,395,348 A | 3/1995 | Ryan |
| 5,398,530 A | 3/1995 | Derman |
| 5,401,245 A | 3/1995 | Haining |
| 5,402,826 A | 4/1995 | Molnar et al. |
| 5,402,982 A | 4/1995 | Atkinson et al. |
| 5,407,437 A | 4/1995 | Heimreid |
| 5,409,471 A | 4/1995 | Atkinson et al. |
| 5,411,483 A | 5/1995 | Loomas et al. |
| 5,411,499 A | 5/1995 | Dudar et al. |
| 5,417,673 A | 5/1995 | Gordon |
| 5,439,451 A | 8/1995 | Collinson et al. |
| 5,439,452 A | 8/1995 | McCarty |
| 5,441,487 A | 8/1995 | Vedder |
| 5,442,941 A | 8/1995 | Kahonan et al. |
| 5,456,676 A | 10/1995 | Nelson et al. |
| 5,470,319 A | 11/1995 | Mayer |
| 5,474,544 A | 12/1995 | Lynn |
| 5,480,393 A | 1/1996 | Bommarito |
| 5,487,731 A | 1/1996 | Denton |
| 5,501,426 A | 3/1996 | Atkinson et al. |
| 5,501,526 A | 3/1996 | Asai et al. |
| 5,509,433 A | 4/1996 | Paradis |
| 5,514,116 A | 5/1996 | Vaillancourt et al. |
| 5,520,665 A | 5/1996 | Fleetwood |
| 5,522,804 A | 6/1996 | Lynn |
| 5,533,708 A | 7/1996 | Atkinson et al. |
| 5,533,996 A | 7/1996 | Murphey et al. |
| 5,535,771 A | 7/1996 | Purdy et al. |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,555,908 A | 9/1996 | Edwards et al. |
| 5,556,388 A | 9/1996 | Johlin, Jr. |
| 5,562,632 A | 10/1996 | Davila et al. |
| 5,569,235 A | 10/1996 | Ross et al. |
| 5,573,516 A | 11/1996 | Tyner |
| 5,577,706 A | 11/1996 | King |
| 5,578,059 A | 11/1996 | Patzer |
| 5,597,536 A | 1/1997 | Mayer |
| 5,603,706 A | 2/1997 | Wyatt et al. |
| 5,609,584 A | 3/1997 | Gettig et al. |
| 5,616,129 A | 4/1997 | Mayer |
| 5,616,130 A | 4/1997 | Mayer |
| 5,617,897 A | 4/1997 | Myers |
| 5,620,424 A | 4/1997 | Abramson |
| 5,620,434 A | 4/1997 | Brony |
| 5,624,414 A | 4/1997 | Boettger |
| 5,632,735 A | 5/1997 | Wyatt et al. |
| 5,639,810 A | 6/1997 | Smith, III et al. |
| 5,660,205 A | 8/1997 | Epstein |
| 5,669,891 A | 9/1997 | Vaillancourt |
| 5,674,206 A | 10/1997 | Allton et al. |
| 5,676,346 A | 10/1997 | Leinsing |
| 5,685,866 A | 11/1997 | Lopez |
| 5,690,612 A | 11/1997 | Lopez et al. |
| 5,690,865 A | 11/1997 | Kindt-Larsen et al. |
| 5,694,686 A | 12/1997 | Lopez |
| 5,695,466 A | 12/1997 | Lopez et al. |
| 5,699,821 A | 12/1997 | Paradis |
| 5,700,248 A | 12/1997 | Lopez |
| 5,728,751 A | 3/1998 | Patnaik |
| 5,730,418 A | 3/1998 | Feith et al. |
| 5,738,663 A | 4/1998 | Lopez |
| 5,749,861 A | 5/1998 | Guala et al. |
| 5,769,825 A | 6/1998 | Lynn |
| 5,775,671 A | 7/1998 | Cote, Sr. |
| 5,776,113 A | 7/1998 | Daugherty et al. |
| 5,782,816 A | 7/1998 | Werschmidt et al. |
| 5,788,215 A | 8/1998 | Ryan |
| 5,797,897 A | 8/1998 | Jepson et al. |
| 5,806,551 A | 9/1998 | Meloul et al. |
| 5,806,831 A | 9/1998 | Paradis |
| 5,807,348 A | 9/1998 | Zinger et al. |
| 5,817,069 A | 10/1998 | Arnett |
| 5,820,601 A | 10/1998 | Mayer |
| 5,833,213 A | 11/1998 | Ryan |
| 5,836,923 A | 11/1998 | Mayer |
| 5,839,715 A | 11/1998 | Leinsing |
| 5,843,046 A | 12/1998 | Motisi et al. |
| 5,846,233 A | 12/1998 | Lilley et al. |
| 5,865,807 A | 2/1999 | Blake, III |
| 5,873,862 A | 2/1999 | Lopez |
| 5,882,348 A | 3/1999 | Winterton et al. |
| 5,899,888 A | 5/1999 | Jepson et al. |
| 5,901,942 A | 5/1999 | Lopez |
| 5,911,710 A | 6/1999 | Barry et al. |
| 5,928,204 A | 7/1999 | Lopez |
| 5,935,620 A | 8/1999 | Baudin |
| 5,947,954 A | 9/1999 | Bonaldo |
| 5,954,313 A | 9/1999 | Ryan |
| 5,957,898 A | 9/1999 | Jepson et al. |
| 5,967,490 A | 10/1999 | Pike |
| 5,979,868 A | 11/1999 | Wu et al. |
| 6,009,902 A | 1/2000 | Troiani et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| 6,048,335 A | 4/2000 | Mayer |
| 6,050,978 A | 4/2000 | Orr et al. |
| 6,063,062 A | 5/2000 | Paradis |
| 6,079,432 A | 6/2000 | Paradis |
| 6,089,541 A | 7/2000 | Weinheimer et al. |
| 6,113,068 A | 9/2000 | Ryan |

| | | |
|---|---|---|
| 6,116,571 A | 9/2000 | Hettinger |
| 6,117,114 A | 9/2000 | Paradis |
| 6,132,403 A | 10/2000 | Lopez |
| 6,132,404 A | 10/2000 | Lopez |
| 6,142,446 A | 11/2000 | Leinsing |
| 6,152,900 A | 11/2000 | Mayer |
| 6,162,206 A | 12/2000 | Bindokas et al. |
| 6,162,251 A | 12/2000 | Kredovski |
| 6,170,800 B1 | 1/2001 | Meloul et al. |
| 6,171,287 B1 | 1/2001 | Lynn et al. |
| 6,177,037 B1 | 1/2001 | Mayer |
| 6,183,448 B1 | 2/2001 | Mayer |
| 6,189,859 B1 | 2/2001 | Rohrbough et al. |
| 6,206,861 B1 | 3/2001 | Mayer |
| 6,210,624 B1 | 4/2001 | Mayer |
| 6,213,996 B1 | 4/2001 | Jepson et al. |
| 6,228,065 B1 | 5/2001 | Lynn |
| 6,228,069 B1 | 5/2001 | Barth et al. |
| 6,245,048 B1 | 6/2001 | Fangrow. et al. |
| 6,254,579 B1 | 7/2001 | Cogger et al. |
| 6,261,282 B1 | 7/2001 | Jepson et al. |
| 6,261,630 B1 | 7/2001 | Nazarova et al. |
| 6,279,783 B1 | 8/2001 | Brown et al. |
| 6,290,206 B1 | 9/2001 | Doyle |
| 6,299,131 B1 | 10/2001 | Ryan |
| 6,299,132 B1 | 10/2001 | Weinheimer |
| 6,325,782 B1 | 12/2001 | Lopez |
| 6,364,869 B1 | 4/2002 | Bonaldo |
| 6,428,520 B1 | 8/2002 | Lopez et al. |
| 6,444,324 B1 | 9/2002 | Yang et al. |
| 6,482,188 B1 | 11/2002 | Rogers et al. |
| D468,016 S | 12/2002 | Mosler et al. |
| 6,541,802 B2 | 4/2003 | Doyle |
| 6,543,745 B1 | 4/2003 | Enerson |
| 6,572,592 B1 | 6/2003 | Lopez |
| 6,585,229 B2 | 7/2003 | Cote, Sr. et al. |
| 6,595,964 B2 | 7/2003 | Finley et al. |
| 6,595,981 B2 | 7/2003 | Huet |
| 6,599,273 B1 | 7/2003 | Lopez |
| 6,605,076 B1 | 8/2003 | Jepson et al. |
| 6,609,696 B2 | 8/2003 | Enerson |
| 6,635,044 B2 | 10/2003 | Lopez |
| 6,651,956 B2 | 11/2003 | Miller |
| 6,656,517 B2 | 12/2003 | Michal et al. |
| 6,669,673 B2 | 12/2003 | Lopez |
| 6,669,681 B2 | 12/2003 | Jepson et al. |
| 6,673,053 B2 | 1/2004 | Wang et al. |
| 6,682,509 B2 | 1/2004 | Lopez |
| 6,689,109 B2 | 2/2004 | Lynn |
| 6,695,817 B1 | 2/2004 | Fangrow, Jr. |
| 6,706,022 B1 | 3/2004 | Leinsing et al. |
| 6,712,791 B2 | 3/2004 | Lui et al. |
| 6,727,294 B2 | 4/2004 | Kanayama et al. |
| 6,740,063 B2 | 5/2004 | Lynn |
| 6,745,998 B2 | 6/2004 | Doyle |
| 6,755,391 B2 | 6/2004 | Newton et al. |
| 6,758,833 B2 | 7/2004 | Lopez |
| 6,783,709 B2 | 8/2004 | Harreld et al. |
| 6,802,490 B2 | 10/2004 | Leinsing |
| 6,808,161 B1 | 10/2004 | Hishikawa |
| 6,840,501 B2 | 1/2005 | Doyle |
| 6,848,139 B2 | 2/2005 | Simon et al. |
| 6,866,656 B2 | 3/2005 | Tingey et al. |
| 6,869,426 B2 | 3/2005 | Ganem |
| 6,871,838 B2 | 3/2005 | Raines et al. |
| 6,883,778 B1 | 4/2005 | Newton et al. |
| 6,892,998 B2 | 5/2005 | Newton |
| 6,908,459 B2 | 6/2005 | Harding et al. |
| 6,916,309 B2 | 7/2005 | Fangrow, Jr. |
| 6,932,795 B2 | 8/2005 | Lopez et al. |
| 6,964,406 B2 | 11/2005 | Doyle |
| 6,991,215 B2 | 1/2006 | Kiehne |
| 6,994,315 B2 | 2/2006 | Ryan et al. |
| 7,014,169 B2 | 3/2006 | Newton et al. |
| 7,025,744 B2 | 4/2006 | Utterberg et al. |
| 7,033,339 B1 | 4/2006 | Lynn |
| 7,037,302 B2 | 5/2006 | Vaillancourt |
| 7,044,441 B2 | 5/2006 | Doyle |
| 7,074,216 B2 | 7/2006 | Fowles et al. |
| 7,100,890 B2 | 9/2006 | Cote et al. |
| 7,104,520 B2 | 9/2006 | Leinsing et al. |
| 7,114,701 B2 | 10/2006 | Peppel |
| 7,125,396 B2 | 10/2006 | Leinsing et al. |
| 7,140,592 B2 | 11/2006 | Phillips et al. |
| 7,184,825 B2 | 2/2007 | Leinsing et al. |
| 7,244,249 B2 | 7/2007 | Leinsing et al. |
| 7,252,652 B2 | 8/2007 | Moorehead et al. |
| 7,264,859 B2 | 9/2007 | Souns et al. |
| 7,306,197 B2 | 12/2007 | Parrino et al. |
| 7,306,199 B2 | 12/2007 | Leinsing et al. |
| 7,314,061 B2 | 1/2008 | Peppel |
| 7,329,249 B2 | 2/2008 | Bonaldo |
| 7,335,182 B1 | 2/2008 | Hilaire |
| 7,357,792 B2 | 4/2008 | Newton et al. |
| 7,396,348 B2 | 7/2008 | Newton et al. |
| 7,422,369 B2 | 9/2008 | Bergman et al. |
| 7,470,261 B2 | 12/2008 | Lynn |
| 7,470,262 B2 | 12/2008 | Hiejima et al. |
| 7,497,848 B2 | 3/2009 | Leinsing et al. |
| 7,497,849 B2 | 3/2009 | Fangrow, Jr. |
| 7,510,545 B2 | 3/2009 | Peppel |
| 7,520,489 B2 | 4/2009 | Rushke |
| 7,530,546 B2 | 5/2009 | Ryan et al. |
| 7,563,243 B2 | 7/2009 | Mendels |
| 7,581,561 B2 | 9/2009 | Funamura et al. |
| 7,584,767 B2 | 9/2009 | Funamura et al. |
| 7,588,563 B2 | 9/2009 | Guala |
| 7,591,449 B2 | 9/2009 | Raines et al. |
| 7,601,141 B2 | 10/2009 | Dikeman et al. |
| 7,615,035 B2 | 11/2009 | Peppel |
| 7,628,774 B2 | 12/2009 | Fangrow, Jr. |
| 7,666,170 B2 | 2/2010 | Guala |
| 7,713,250 B2 | 5/2010 | Harding et al. |
| 7,717,886 B2 | 5/2010 | Lopez |
| 7,753,338 B2 | 7/2010 | Desecki |
| 7,753,892 B2 | 7/2010 | Newton et al. |
| 7,758,566 B2 | 7/2010 | Simpson et al. |
| 7,763,199 B2 | 7/2010 | Fangrow |
| 7,784,766 B2 | 8/2010 | Guala |
| 7,815,168 B2 | 10/2010 | Vangsness et al. |
| 7,824,393 B2 | 11/2010 | Fangrow, Jr. |
| 7,837,658 B2 | 11/2010 | Cote, Sr. et al. |
| 7,857,284 B2 | 12/2010 | Kimball et al. |
| 7,857,285 B2 | 12/2010 | Lee et al. |
| 7,867,204 B2 | 1/2011 | Bartholomew et al. |
| 7,879,012 B2 | 2/2011 | Kane et al. |
| 7,914,502 B2 | 3/2011 | Newton et al. |
| 7,975,722 B2 | 7/2011 | Kiehne |
| 7,998,134 B2 | 8/2011 | Fangrow |
| D644,731 S | 9/2011 | Fangrow, Jr. |
| 8,105,314 B2 | 1/2012 | Fangrow |
| 8,221,391 B2 | 7/2012 | Fangrow, Jr. |
| 2001/0049508 A1 | 12/2001 | Fangrow, Jr. |
| 2002/0120333 A1 | 8/2002 | Keogh et al. |
| 2004/0006330 A1 | 1/2004 | Fangrow, Jr. |
| 2005/0020981 A1 | 1/2005 | Kurth |
| 2005/0038397 A1* | 2/2005 | Newton et al. ............... 604/249 |
| 2005/0059952 A1 | 3/2005 | Giuliano et al. |
| 2005/0121638 A1 | 6/2005 | Doyle |
| 2005/0222541 A1 | 10/2005 | Lopez et al. |
| 2006/0004331 A1 | 1/2006 | Fangrow, Jr. |
| 2006/0161115 A1 | 7/2006 | Fangrow, Jr. |
| 2006/0200088 A1 | 9/2006 | Lopez |
| 2006/0200089 A1 | 9/2006 | Lopez et al. |
| 2006/0200090 A1 | 9/2006 | Lopez et al. |
| 2006/0206061 A1 | 9/2006 | Lopez et al. |
| 2006/0211997 A1 | 9/2006 | Fangrow, Jr. |
| 2006/0211998 A1 | 9/2006 | Fangrow, Jr. |
| 2006/0211999 A1 | 9/2006 | Fangrow, Jr. |
| 2006/0212001 A1 | 9/2006 | Fangrow, Jr. |
| 2006/0212003 A1 | 9/2006 | Fangrow, Jr. |
| 2006/0212006 A1 | 9/2006 | Fangrow, Jr. |
| 2006/0224127 A1 | 10/2006 | Fangrow, Jr. |
| 2006/0264842 A1 | 11/2006 | Fangrow, Jr. |
| 2006/0264844 A1 | 11/2006 | Fangrow, Jr. |
| 2006/0264849 A1 | 11/2006 | Lopez et al. |
| 2006/0264909 A1 | 11/2006 | Fangrow, Jr. |
| 2006/0264910 A1 | 11/2006 | Fangrow, Jr. |

| | | | | | | |
|---|---|---|---|---|---|---|
| 2006/0270999 | A1 | 11/2006 | Fangrow, Jr. | EP | 0 263 789 | 4/1988 |
| 2006/0271016 | A1 | 11/2006 | Fangrow, Jr. | EP | 0 309 771 | 4/1989 |
| 2006/0276757 | A1 | 12/2006 | Fangrow, Jr. | EP | 0 399 119 | 11/1990 |
| 2006/0276758 | A1 | 12/2006 | Fangrow, Jr. | EP | 0 446 463 | 9/1991 |
| 2007/0100284 | A1 | 5/2007 | Leinsing et al. | GB | 2 000 685 | 1/1979 |
| 2007/0106205 | A1 | 5/2007 | Connell et al. | GB | 2 034 185 | 6/1980 |
| 2007/0112312 | A1 | 5/2007 | Fangrow, Jr. | WO | WO 92/20736 | 11/1992 |
| 2007/0112313 | A1 | 5/2007 | Fangrow, Jr. | WO | WO 99/59672 | 11/1999 |
| 2007/0224865 | A1 | 9/2007 | Fangrow, Jr. | WO | WO 99/61093 | 12/1999 |
| 2007/0225425 | A1 | 9/2007 | Nash et al. | WO | WO 03/018104 | 3/2003 |
| 2007/0235676 | A1 | 10/2007 | Vangsness et al. | WO | WO 2005/115521 | 8/2005 |
| 2007/0254000 | A1 | 11/2007 | Guo et al. | WO | WO 2006/013433 | 2/2006 |
| 2007/0270756 | A1 | 11/2007 | Peppel et al. | WO | WO 2006/062912 | 6/2006 |
| 2008/0039802 | A1 | 2/2008 | Vangsness et al. | WO | WO 2008/048777 | 4/2008 |
| 2008/0086097 | A1 | 4/2008 | Rasmussen et al. | | | |
| 2008/0086099 | A1 | 4/2008 | McKinnon et al. | | | |
| 2008/0097407 | A1 | 4/2008 | Plishka | | | |
| 2008/0249508 | A1 | 10/2008 | Lopez et al. | | | |
| 2009/0209922 | A1 | 8/2009 | Boisjoly | | | |
| 2009/0292252 | A1 | 11/2009 | Lareau et al. | | | |
| 2010/0036330 | A1 | 2/2010 | Plishka et al. | | | |
| 2010/0059702 | A1 | 3/2010 | Mansour et al. | | | |
| 2010/0174242 | A1 | 7/2010 | Anderson et al. | | | |
| 2010/0249723 | A1 | 9/2010 | Fangrow, Jr. | | | |
| 2010/0249724 | A1 | 9/2010 | Cote, Sr. et al. | | | |
| 2010/0249725 | A1 | 9/2010 | Cote, Sr. et al. | | | |
| 2010/0264343 | A1 | 10/2010 | Jeory | | | |
| 2011/0028915 | A1 | 2/2011 | Siopes et al. | | | |
| 2011/0046572 | A1 | 2/2011 | Fangrow | | | |
| 2011/0282302 | A1 | 11/2011 | Lopez et al. | | | |

FOREIGN PATENT DOCUMENTS

| | | |
|---|---|---|
| CA | 2 175 021 | 11/1996 |
| CH | 636526 | 6/1983 |
| CH | 670955 | 7/1989 |
| DE | 855 319 | 9/1952 |
| DE | 84 25 197.2 | 9/1985 |
| DE | 37 40 269 | 6/1989 |

OTHER PUBLICATIONS

U.S. Appl. No. 10/217,213, filed Dec. 16, 1996, Fangrow et al.
Capless Backcheck Valve dated Sep. 3, 1993.
F.D.A. 510(k) Summary of Safety and Effectiveness dated Nov. 17, 1997.
Saechtling Tworzywa Sztuczne, WN-T Warszawa, 1999, V edition, pp. 224-225.
PASV Valve Connector Brochure, which appears to be at least as early as Feb. 20, 2001.
LifeShield TKO Anti-Reflux Device Brochure dated Feb. 8, 2008.
"Faulding Inc. receives FDA permission to market patented Safe-Connect Valve", dated Dec. 2, 1996.
MicroClave Connector Brochure. The MicroClave was available before Mar. 25, 2008.
MEDI-4955 Liquid Silicone Rubber from NuSil Silicone Technology, dated Dec. 17, 2010.
International Search Report and Written Opinion, re App. No. PCT/US2007/082570, mailed Apr. 2, 2008.

* cited by examiner

MEDICAL CONNECTOR

CROSS-REFERENCE TO RELATED APPLICATIONS

This application is a continuation of U.S. patent application Ser. No. 11/924,494, filed Oct. 25, 2007 (entitled "MEDICAL CONNECTOR"), now U.S. Pat. No. 8,105,314, which claims the benefit of U.S. Provisional Patent Application No. 60/854,524, filed Oct. 25, 2006 (entitled "MEDICAL CONNECTOR"), the entire disclosure of each being hereby incorporated herein by reference.

BACKGROUND OF THE INVENTION

1. Field of the Invention

The inventions relate generally to medical connectors. In particular, certain embodiments of the inventions relate to medical connectors for use with standard luer connectors. In certain embodiments, the medical connectors generate a positive flow of fluid away from a medical implement as the implement is removed from an end or port of the medical connector.

2. Description of the Related Art

Medical connectors are often used to selectively open and close fluid pathways for use in treating patients. In some connectors, a small amount of retrograde fluid flow occurs when the connector is closed, drawing fluid away from the patient and toward the connector. This retrograde flow can lead to clotting or obstructions in the fluid line, effectively shortening the time period during which a particular injection point is useable. In many applications, it is advantageous to minimize or eliminate such retrograde flow or to produce a positive flow of fluid toward the patient as the valve closes.

U.S. Pat. No. 6,599,273 (incorporated herein in its entirety) includes a general description of some examples of medical connectors in which retrograde fluid flow may occur. U.S. Pat. Nos. 6,245,048, 6,428,520, 6,695,817, and U.S. Patent Application Publication No. 2006-0161115A1 (incorporated herein in their entireties) include general descriptions of some examples of medical valves in which a positive flow of fluid is produced away from the medical connector and toward the patient as the connector closes. There are many different types of medical connectors, and the foregoing patents are cited merely to illustrate some ways in which fluid can be transferred through connectors. The methods, structures, and principles disclosed herein can be used in or adapted to function with the connectors (and components thereof) disclosed in the foregoing patents as well as in many different types of medical connectors known or used in this field.

SUMMARY OF THE INVENTION

In some embodiments, a medical connector for use with a first and second medical implement is described including a housing having a first proximal end and a second distal end, each configured for attachment to standard luer connectors. In some embodiments, the connector further includes an inner rigid element extending within the housing having at least one opening on a side thereof. The inner rigid element may be substantially hollow in its interior with the said opening extending from an outer surface of the inner rigid element to the hollow interior. A substantially hollow flexible element may be positioned within the housing substantially surrounding the inner rigid element. The flexible element may include at least one inward projection on an inner wall thereof, wherein at least a portion of the inward projection may be shaped to cooperate with the opening in the inner rigid element such that when the connector is in a substantially closed position, wherein fluid is not permitted to flow through the connector, the portion of the inward projection is within the opening and when the connector is in a substantially open position, the portion of the inward projection is outside of the opening to permit a reduction in the inner volume of the flexible element and/or the interior of the inner rigid element when the connector is in the substantially closed position.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which.

DETAILED DESCRIPTION OF THE PREFERRED EMBODIMENT

While the description sets forth various embodiment specific details, it will be appreciated that the description is illustrative only and should not be construed in any way as limiting the invention. Furthermore, various applications of the invention, and modifications thereto, which may be apparent to those who are skilled in the art, are also encompassed by the general concepts described herein. For example, any of the structures in the devices illustrated or described in the patent documents incorporated herein by reference may be combined with or used instead of the structures disclosed herein.

Figure 1:
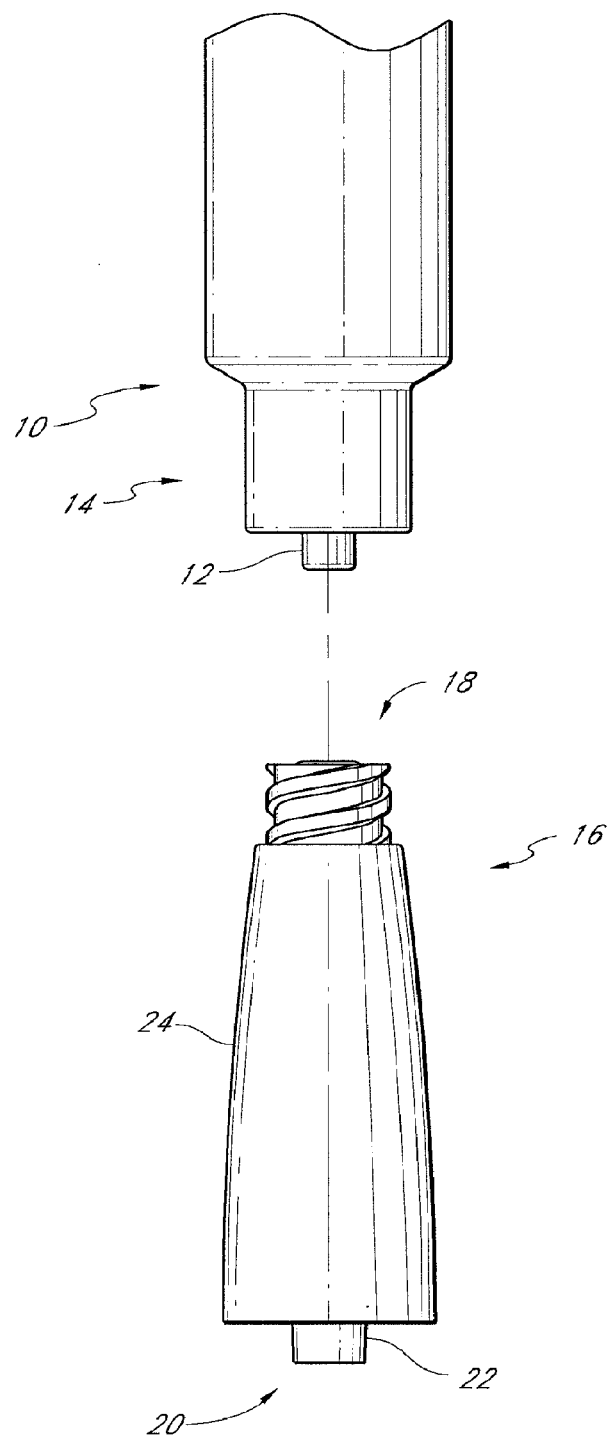
FIG. 1 is a side view of a medical connector in a first position and a medical implement according to some embodiments of these inventions.
Figure 2:
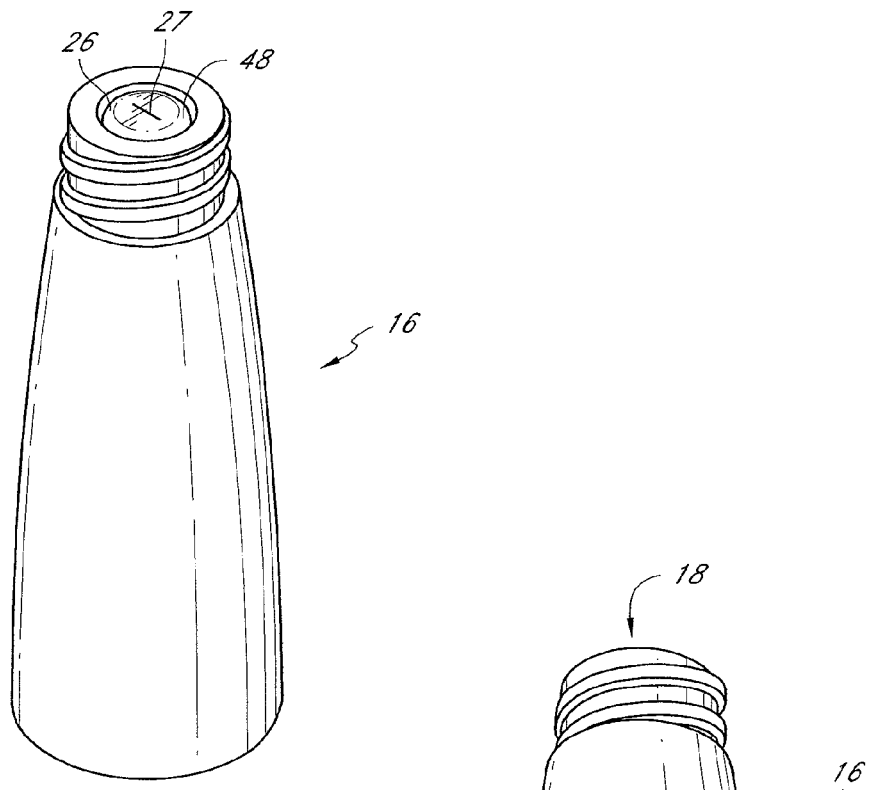
FIG. 2 is a top perspective view of the medical connector of FIG. 1.
Figure 3:
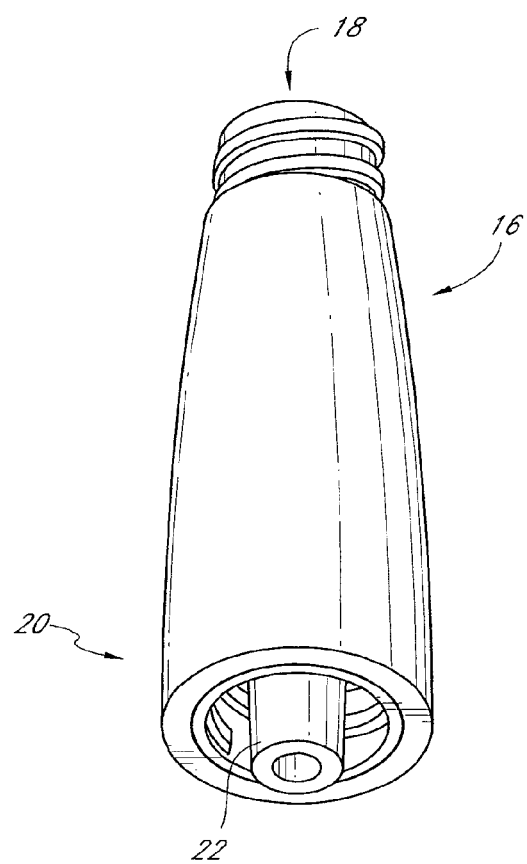
FIG. 3 is a bottom perspective view of the medical connector of FIG. 1.

FIG. 1 illustrates a male luer connector 10 with a luer end 12 and a luer lock 14 approaching a female connector 16. The female connector 16 has a proximal end 18, a distal end 20, with a male luer 22 on its distal end. The distal end 20 may further include a luer lock. The female connector 16 includes a housing 24. FIG. 2 illustrates a perspective view of the female connector 16. The proximal end 48 of a flexible element 26 is illustrated. The flexible element 26 may include an orifice 27 that is normally closed until a distally directed force is applied to flexible element 26. FIG. 3 illustrates a perspective view of the connector 16 in which the male luer 22 on the distal end 20 of the connector is visible.

Figure 4:
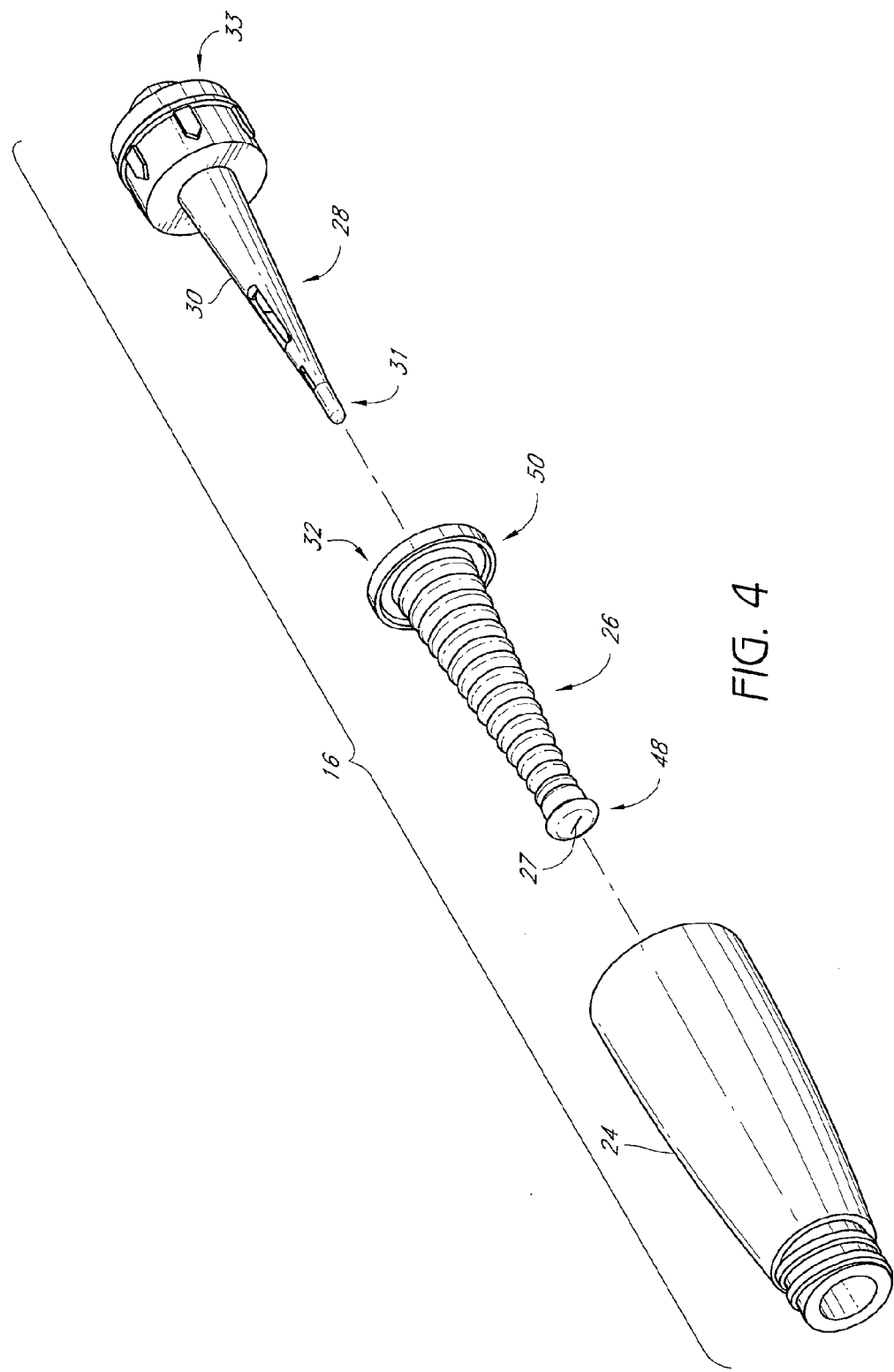
FIG. 4 is an exploded perspective view of the medical connector of FIG. 1.

FIG. 4 is an exploded perspective view of the connector 16 of FIG. 2. Some of the internal components of connector 16 are illustrated, such as flexible element 26 and rigid element 28. In some embodiments of the assembled configuration, an inner rigid element 30 is provided and can fit within a cavity 32 inside of flexible element 26. Orifice 27 is shown closed in this exploded perspective view. In some embodiments, orifice 27 is open when flexible element 26 is separate from housing 24. In some embodiments, contact between the inner cavity of the housing 24 and portions of the proximal end 48 of flexible element 26 upon insertion of flexible element 26 into housing 24 may cooperate to substantially close orifice 27 such that the fluid flow path through connector 16 is impeded.

Figure 5:
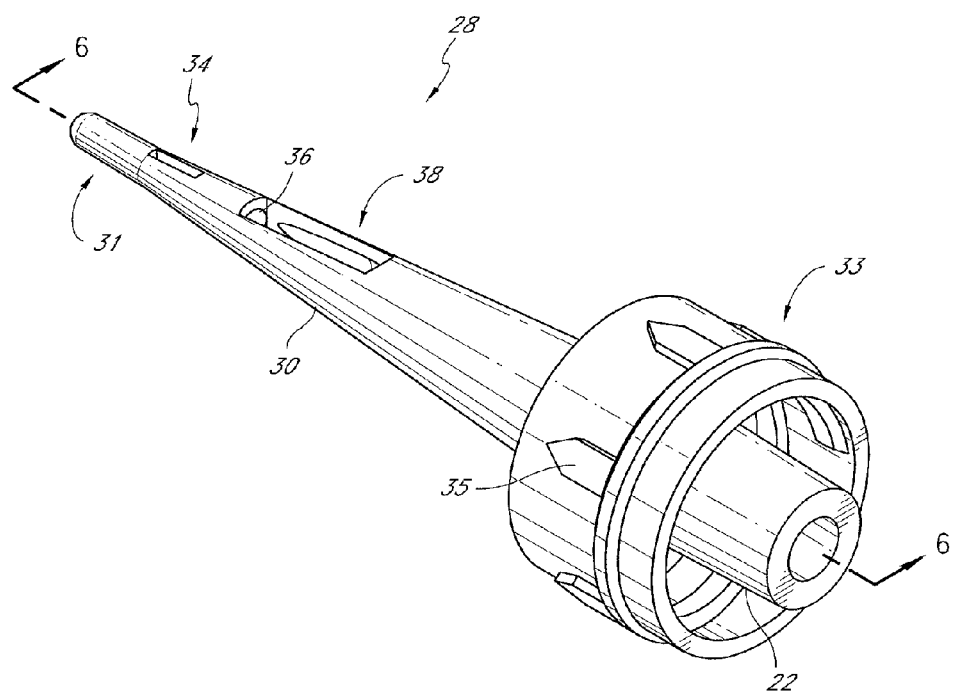
FIG. 5 is a bottom perspective view of a component of a medical connector according to some embodiments of these inventions.

FIG. 5 illustrates a perspective view of rigid element 28 having a proximal end 31 and a distal end 33. Distal end 33 may include radially projecting elements 35. Radial elements 35 interact with corresponding features in the internal wall of housing 24 to secure rigid element 28 within housing 24 upon assembly of the connector 16. Radial elements 35 extending along the longitudinal axis of connector 16 may interact with housing 24 to inhibit rotation of rigid element 28 inside of housing 24 when connector 16 is manipulated, for example when a female connector is attached to the distal end 20 of connector 16.

In some embodiments, inner rigid element 30 has multiple openings. For example, openings 34 can be used to permit fluid to flow into an internal passage or fluid-flow path 36 inside of inner rigid element 30. In some embodiments, two openings 34 are disposed on opposite sides of inner rigid element 30. Additional openings similar to opening 34 can also be provided. In some embodiments, an opening can be provided at the proximal end 31 of inner rigid element 30. In some embodiments, one or more of openings 34 and 38 are combined (i.e., the same openings(s) are configured to receive fluid and to receive one or more protrusions 52 (see FIG. 7A). Inner rigid element 30 may be blunt, pointed, opened-ended, closed-ended, or shorter or longer, or wider or narrower than shown here. Inner rigid element 30 may have many different shapes. For example, it may be configured as a tube-like structure as shown, configured as a sleeve with one or more longitudinal openings or slits extending partially along the length of the sleeve or along the entire length of the sleeve, or the inner rigid element 30 may be eliminated entirely. Inner rigid element 30 may be in a fixed position inside of the housing 24 or it may be moveable or floating inside of the housing 24. In the absence of inner rigid element 30, one or more fluid openings may be provided at or near a distal region of the cavity inside the housing to convey fluid within the housing cavity to the male end of the connector.

In some embodiments, one or more openings 38 are provided in inner rigid element 30, and may be located in a direction distal from opening 34. As will be described below, in some embodiments, opening 38 is intended to receive a protrusion on an internal surface of flexible element 26 when the connector 16 is in the closed configuration (see FIG. 8A). In some embodiments, opening 38 is adapted to receive fluid flow. Where opening 38 is used to facilitate fluid flow through inner rigid element 30, opening 34 may or may not be included.

Figure 6A:
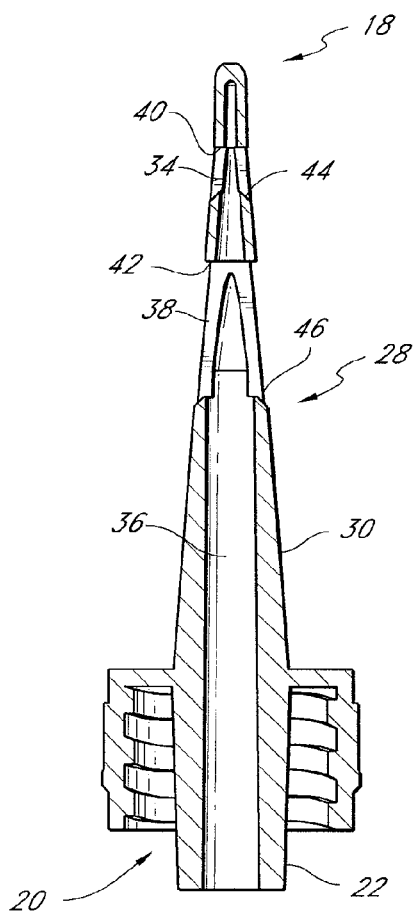
FIG. 6A is a cross-sectional view of the medical connector component of FIG. 5.
Figure 6B:
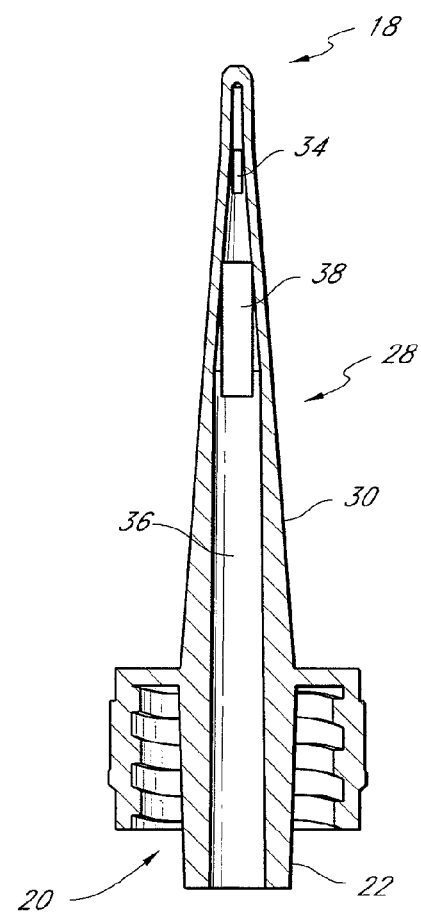
FIG. 6B is a cross-sectional view of the medical connector component of FIG. 6A rotated 90 degrees.

FIGS. 6A and 6B illustrate orthogonal cross-sections of rigid element 28 taken in a vertical plane. In some embodiments, as illustrated, the proximal edges 40, 42 of openings 34, 38 can be flat and substantially horizontal, and the distal edges 44, 46 of openings 34, 38 can be slanted or beveled.

As illustrated, the fluid-flow path 36 may extend from the proximal end of the inner rigid element 30 along a generally axially-oriented linear path to the male end 22. In some embodiments, as illustrated, the fluid-flow path 36 in the distal region of the inner rigid element 30 is generally non-tortuous; for example, the fluid-flow path 36 may not turn in a direction that is perpendicular to or substantially non-parallel with the axis of the inner rigid element 30, and/or it may not include fluid-exiting side openings in the distal region of the inner rigid element 30. Such a fluid-flow path may provide a higher fluid flow rate and create less turbulence in the fluid flow (which can be especially advantageous when the fluid includes blood cells).

Figure 7A:
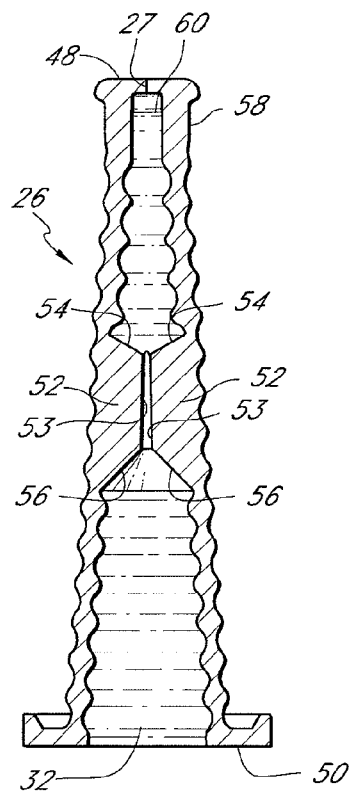
FIG. 7A is a cross-sectional view of a component for a medical connector according to some embodiments of these inventions.
Figure 7B:
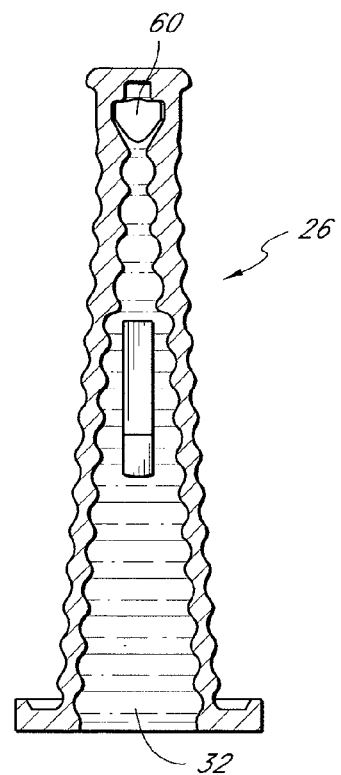
FIG. 7B is a cross-sectional view of the medical connector component of FIG. 7A rotated 90 degrees.

FIGS. 7A and 7B illustrate orthogonal cross-sections of flexible element 26 taken in a vertical plane. Flexible element 26 can be longitudinally compressed and/or moved by a force applied to the proximal end 48 toward the distal end 50. A plurality of inwardly projecting elements 52 are provided in an internal cavity 32 of flexible element 26. In some embodiments, there is one such protrusion 52. In the illustrated embodiment, there are two protrusions 52. In some embodiments, there can be multiple openings 38, some of which can be positioned along different regions of inner rigid element 30, and there can be additional corresponding protrusions 52 that can be designed to selectively fit within or be withdrawn from one or more openings 38. In some embodiments, as shown, the internal edges or faces 53 of the opposing protrusions 52 can be positioned and oriented to contact each other and/or be close to each other when the connector 16 is in a substantially closed position. The protrusions 52 can extend into the inner rigid element 30 at an intermediate position within the fluid-flow path 36 of the inner rigid element 30. In some embodiments, the wall of the inner rigid element 30 is not positioned between the opposing edges or faces 53 of the protrusions 52 in the substantially opened position. Openings 38 can have a variety of different shapes and sizes. For example, one or more of openings 38 can be round, square, rectangular, trapezoidal, elliptical, etc. Opening 38 can be larger than opening 34. In some embodiments, opening 38 can be approximately at least one-fifth, one-quarter, one-third, one-half, or more of the length of inner rigid element 30. Protrusions 52 can also have a variety of different shapes and sizes, which may correspond to or be different from the shapes and/or sizes of openings 38. As shown, the protrusions 52 can be substantially planar. In some embodiments, the volume of the one or more protrusions 52 can be approximately equivalent to or greater than the volume in the proximal region of the connector adapted to receive the luer 12.

In some embodiments, upper or proximal edges 54 of protrusions 52 can be slanted and/or beveled. Similarly, lower or distal edges 56 of protrusions 52 can be also slanted and/or beveled. Slanting or beveling these surfaces may facilitate fluid flow through the connector 16 and may minimize turbulence in the fluid flow. In general, the shape, materials, and structure of rigid element 28 and flexible element 26 can be selected to allow protrusions 52 to be positioned within openings 38 when the connector is closed, and protrusions 52 can be completely or partially withdrawn from openings 38 when the connector is opened. When the connector 16 is in the substantially closed position, the inward protrusions 52 function so as to reduce the fluid space within the connector 16 and the fluid flow path as compared to when the connector 16 is in the substantially open position.

In some embodiments, flexible element 26 can be made of silicon, and the remaining components of connector 16 can be made of a polymer material such as polycarbonate. A proximal region 58 of flexible element 26 can include a portion with an increased wall thickness or a structure (or materials of composition) that contribute to the proximal region 58 being stiffer or harder than the portion of the flexible element 26 that flexes during compression. By providing increased stiffness or hardness for the proximal region 58, there is a lower likelihood that fluid within the valve will be forced back into the fluid path 32 inside of flexible element 26 as flexible element 26 expands to its original height when the valve is closed. Moreover, in some embodiments, a proximal portion 60 of fluid pathway 32 inside the flexible element 26 has a horizontal cross-sectional area that is substantially less than the horizontal cross-sectional area of a region in the fluid path 36 of element 28, so that fluid flow out of the distal end of the connector is encouraged and retrograde fluid flow toward the proximal end of the connector is discouraged.

In some embodiments, orifice 27 extends along an axis substantially perpendicular to inward projections 52, as shown in FIG. 7A. In other embodiments, orifice 27 extends along substantially the same plane as projections 52.

As shown in FIGS. 7A and B, proximal portion 60 may include a non-rotationally symmetrical cross-sectional diameter. In some embodiments, the proximal portion 60 has smaller cross-sectional diameter in the plane perpendicular to orifice 27 and a larger cross-sectional diameter in the plane of orifice 27. In some embodiments, portions of proximal portion 60 have a substantially rectangular cross-sectional area.

Figure 8A:
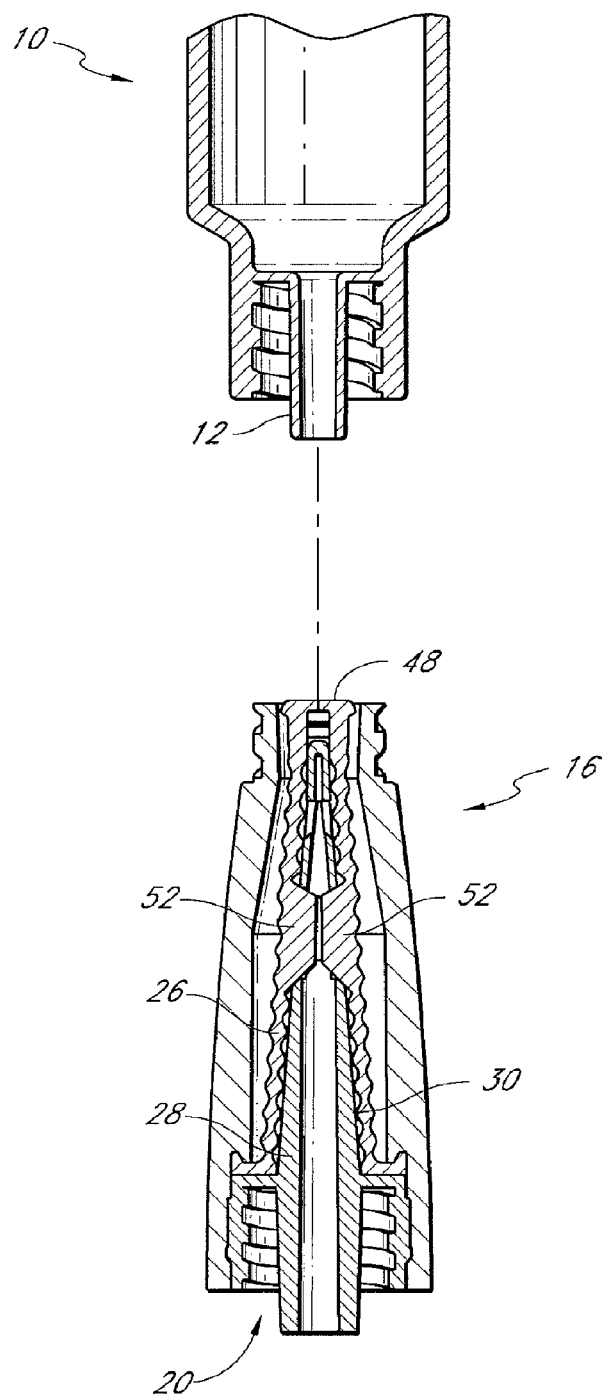
FIG. 8A is a cross-sectional view of a medical connector in a first position and a medical implement according to some embodiments of these inventions.
Figure 8B:
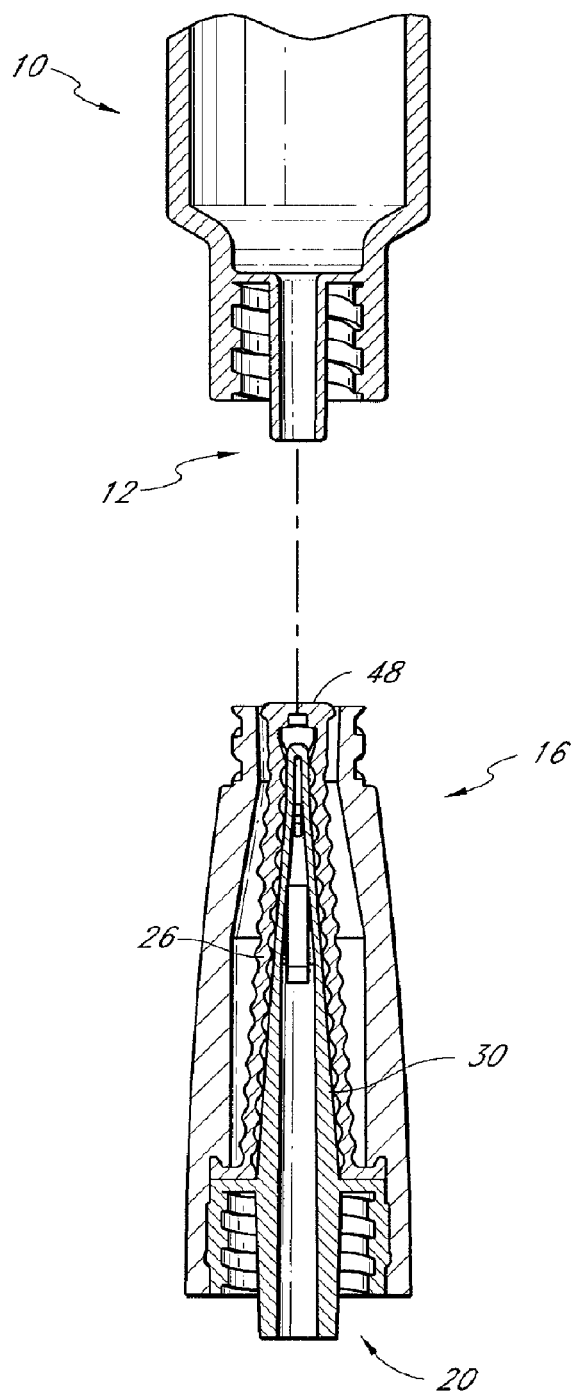
FIG. 8B is a cross-sectional view of the medical connector and medical implement of FIG. 8A rotated 90 degrees.

FIG. 8A illustrates a vertical cross-section of the male luer 10 and female connector 16 illustrated in FIG. 1. In FIGS. 8A and 8B, a portion of rigid element 28 is positioned within the internal cavity 32 of flexible element 26. Inward protrusions 52 are positioned within openings 38, and more particularly, in the fluid flow path through connector 16. Fluid flow within connector 16 is substantially occluded. The proximal end 48 of flexible element 26 may be swabbable with antiseptic in a sweeping motion across the proximal end 18 of the connector 16, and the proximal end 48 may extend above the housing, may be substantially flush with the housing, or may be recessed within the housing.

Figure 9A:
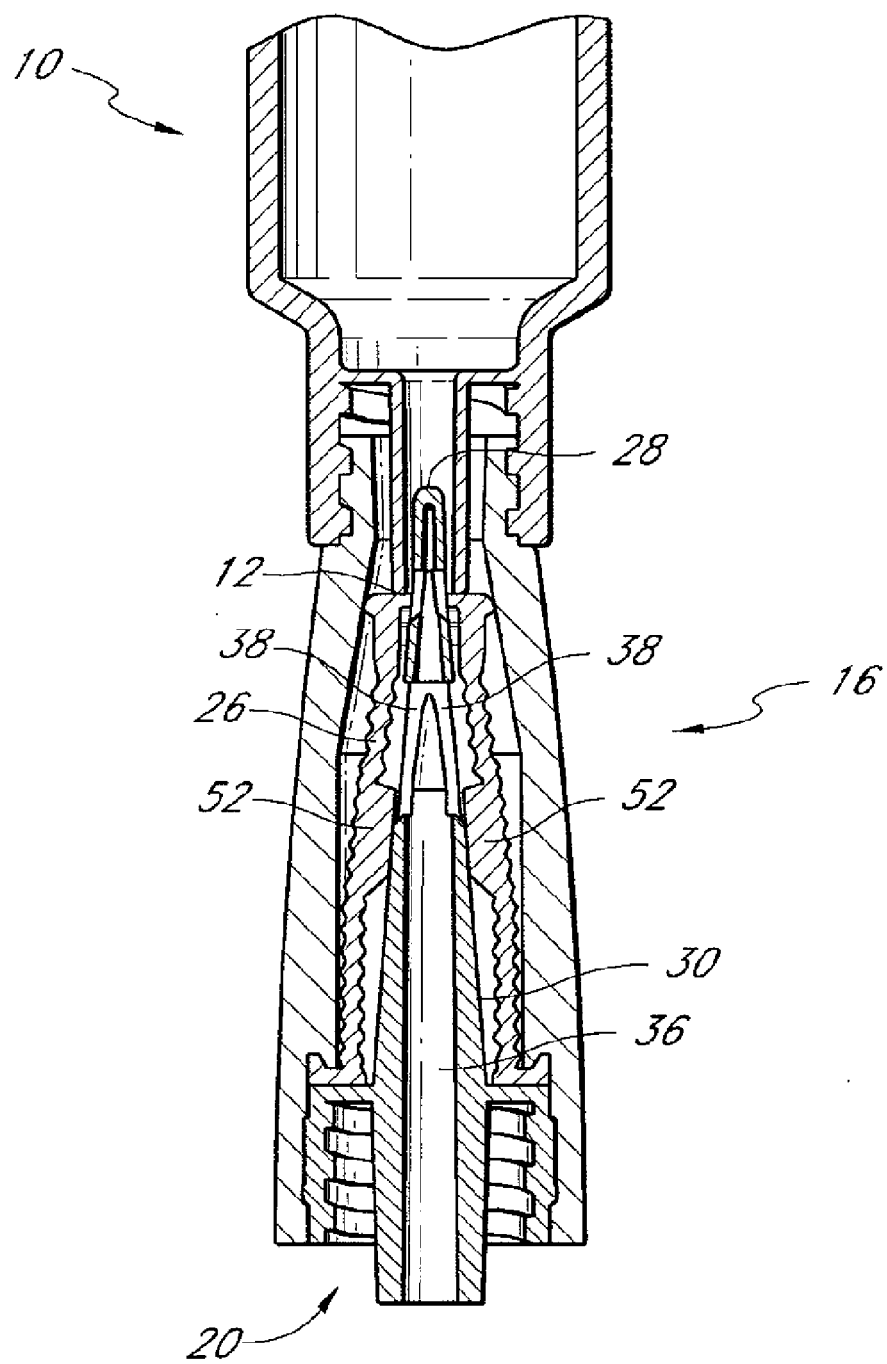
FIG. 9A is a cross-sectional view of a medical connector engaged with a medical implement according to some embodiments of these inventions.
Figure 9B:
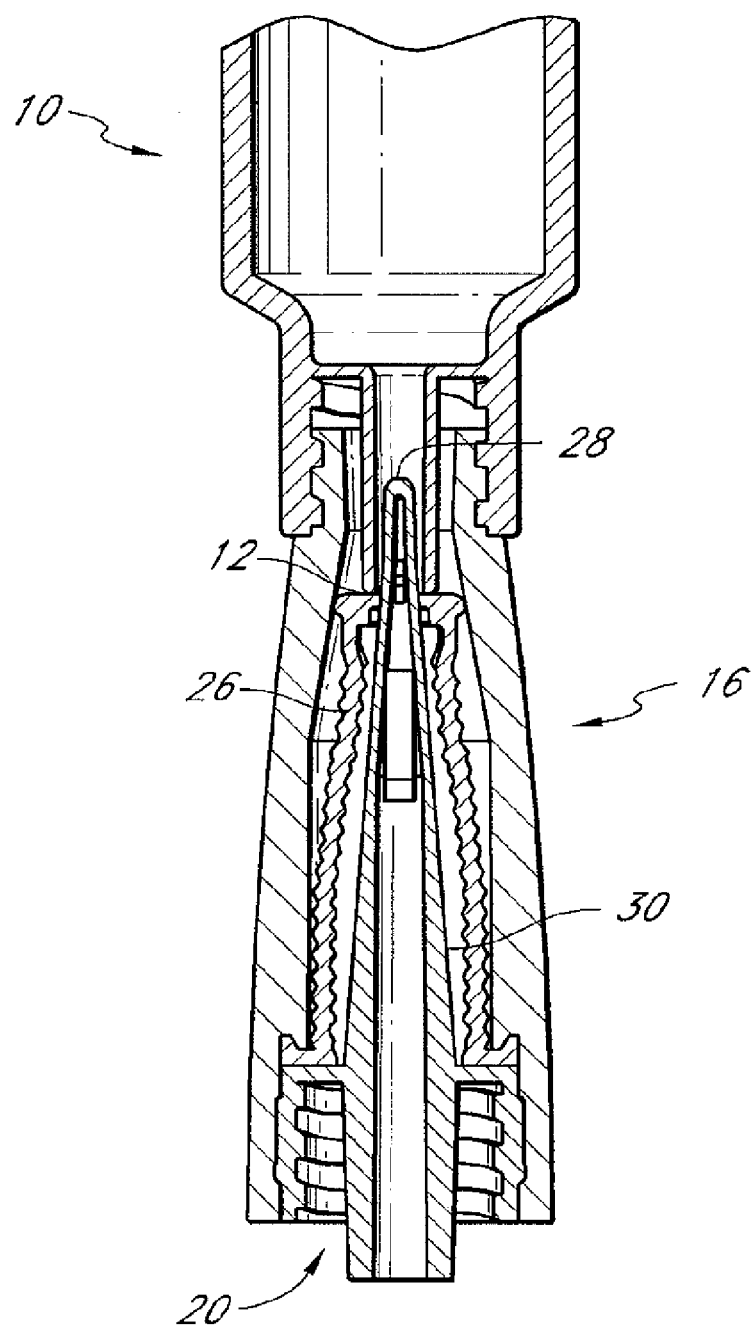
FIG. 9B is a cross-sectional view of the medical connector and medical implement of FIG. 9A rotated 90 degrees.

FIGS. 9A and 9B illustrate an embodiment of the female connector 16 after it is connected to the male luer connector 10 in orthogonal vertical cross-sections. In some embodiments, flexible element 26 can be compressed and/or moved by a distally directed force applied by the male luer 12. As shown, a portion of inner rigid element 30 can extend in a proximal direction beyond orifice 27 during compression. In some embodiments, inner rigid element 30 does not extend further in a proximal direction than the proximal end 48 of the flexible element 26 when compressed. In some embodiments, orifice 27 may automatically open to allow fluid flow through the connector 16 upon insertion of the male luer connector 10 into connector 16.

In FIGS. 9A and 9B, the medical connector 16 is substantially open to fluid flow between the male luer 10 and the distal end 20 of the female connector 16. As shown in FIG. 9A, the protrusions 52 can be partially or completely withdrawn from the openings 38 so that the volume inside of the fluid path 36 during the open stage of the connector 16 is substantially larger than the fluid volume inside of the fluid path 36 when the connector 16 is closed (see, e.g., FIG. 8A). This can diminish, or eliminate, retrograde fluid flow from the patient toward the proximal end 18 of the connector 16, or even produce a positive flow of fluid upon closure in the direction of the distal end 20 of the connector 16 and toward the patient. In some embodiments, proximal region 58 resists compression to a greater extent than a region on flexible element 26 positioned distal from the region 58 during the insertion of the mail luer connector 10 into the female connector 16. Proximal region 58 can substantially maintain its height, before and after compression and/or movement, as fluid flow is enabled through the connector 16, which may reduce any vacuum effect in this portion of flexible element 26.

The foregoing description is provided to illustrate certain examples. The inventive concepts, principles, structures, steps, and methods disclosed herein can be applied to the devices and methods disclosed in the attached patents and in many other types of medical connectors.

The invention claimed is:

1. A method of transferring fluid from a first medical implement to a second medical implement, the method comprising:
providing a medical connector having a housing with a proximal end and a proximal opening and a distal end and a distal opening, an inner rigid element positioned within said housing and including an inner surface defining a substantially hollow interior, a first inner opening on said inner surface, an outer surface, a first outer opening on said outer surface, a first passage extending between said first inner opening and said first outer opening, and a substantially hollow flexible element positioned within said housing, said flexible element comprising an orifice on a proximal surface, said orifice generally closed with said flexible element in a first position and generally open with said flexible element in a second position, and at least one inward projection on an inner wall thereof, at least a portion of said at least one inward projection projecting through said first outer opening, said first passage, and said first inner opening when said flexible element is in said first position, thereby occupying at least a portion of said substantially hollow interior of said inner rigid element;
coupling said distal end of said housing to a second medical implement;
coupling said proximal end of said housing to a first medical implement wherein a distal end of said first medical implement enters said proximal opening of said housing;
displacing said flexible element by distally delivering said first medical implement within said housing and pushing said flexible element into said second position, wherein said proximal surface of said flexible element is displaced from said proximal opening and said at least one inward projection of said flexible element is displaced from said substantially hollow interior of said inner rigid element; and
establishing fluid communication between said first medical implement and said second medical implement.

2. The method of transferring fluid of claim 1, wherein said at least one inward projection is external to said inner rigid element when said flexible element is in said second position.

3. The method of transferring fluid of claim 1, wherein a proximal end of said inner rigid element extends through said orifice of said flexible element in said second position.

4. The method of transferring fluid of claim 1, further comprising said step of decoupling said housing and said second medical implement, whereby said flexible element returns to said first position and said at least one inward projection extends through said first outer opening, said first passage, and said first inner opening, thereby occupying said portion of said substantially hollow interior of said inner rigid element.

5. The method of transferring fluid of claim 4, wherein a volume of said at least one inward projection projecting through said first outer opening, said first passage, and said first inner opening substantially eliminates a flow of fluid into said distal end of said housing as said flexible element transitions from said second position to said first position.

6. The method of transferring fluid of claim 1, wherein said at least one inward projection comprises a slanted surface on a distal side thereof to facilitate said movement of said portion of said at least one inward projection into and out of said first outer opening in said inner rigid element.

7. The method of transferring fluid of claim 6, wherein a distal side of said first passage in said inner rigid element comprises a slanted portion cooperating with said distal side of said at least one inward projection to further facilitate said movement of said portion of said at least one inward projection into and out of said first outer opening in said inner rigid element.

* * * * *